(12) United States Patent
Liu et al.

(10) Patent No.: US 10,370,352 B2
(45) Date of Patent: Aug. 6, 2019

(54) CYCLOBUTYL-IMIDAZOLIDINONE COMPOUNDS

(71) Applicant: Eli Lilly and Company, Indianapolis, IN (US)

(72) Inventors: Lian Zhu Liu, Indianapolis, IN (US); Haizhen Zhang, Indianapolis, IN (US); Xiaoqing Wang, Indianapolis, IN (US); Gang Liu, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 16/123,916

(22) Filed: Sep. 6, 2018

(65) Prior Publication Data

US 2019/0071413 A1    Mar. 7, 2019

(30) Foreign Application Priority Data

Sep. 7, 2017  (CN) .............................. 2017 1 00858
Aug. 14, 2018  (CN) .............................. 2018 1 00515

(51) Int. Cl.
*A61P 1/16*      (2006.01)
*C07D 401/04*   (2006.01)

(52) U.S. Cl.
CPC .............. *C07D 401/04* (2013.01); *A61P 1/16* (2018.01)

(58) Field of Classification Search
CPC .................................................. C07D 401/04
See application file for complete search history.

(56) References Cited

U.S. PATENT DOCUMENTS

| 8,742,126 B2 | 6/2014 | Notte |
| 2015/0342943 A1 | 12/2015 | Bornstein et al. |
| 2017/0173031 A1 | 6/2017 | Notte |

FOREIGN PATENT DOCUMENTS

| WO | WO-2002/039987 A2 | 5/2002 |
| WO | WO-2012/003387 A1 | 1/2012 |
| WO | WO-2013/112741 | 8/2013 |
| WO | WO-2013/112741 A1 | 8/2013 |
| WO | WO-2016/049069 A1 | 3/2016 |

OTHER PUBLICATIONS

Bastin, R.J. et al. (Jul. 19, 2000). "Salt Selection and Optimization Procedures for Pharmaceutical New Chemical Entities," *Org. Proc. Res. Dev.* 4(5):427-435.
Berge, S.M. et al. (Jan. 1977). "Pharmaceutical Salts," *J. Pharm. Sci.* 66(1):1-19.
Gould, P.L. (Nov. 1986). "Salt Selection for Basic Drugs," *International Journal of Pharmaceutics* 33(1-3):201-217.

(Continued)

*Primary Examiner* — Joseph R Kosack
(74) *Attorney, Agent, or Firm* — Morrison & Foerster LLP

(57) ABSTRACT

The present invention provides a compound of Formula I

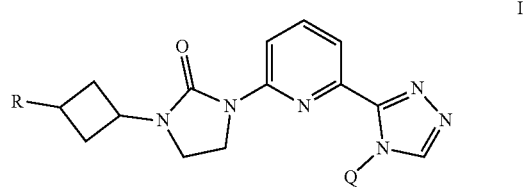

wherein
Q is selected from the group consisting of —CH(CH$_3$)$_2$ and

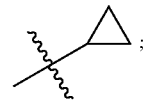

R is selected from the group consisting of

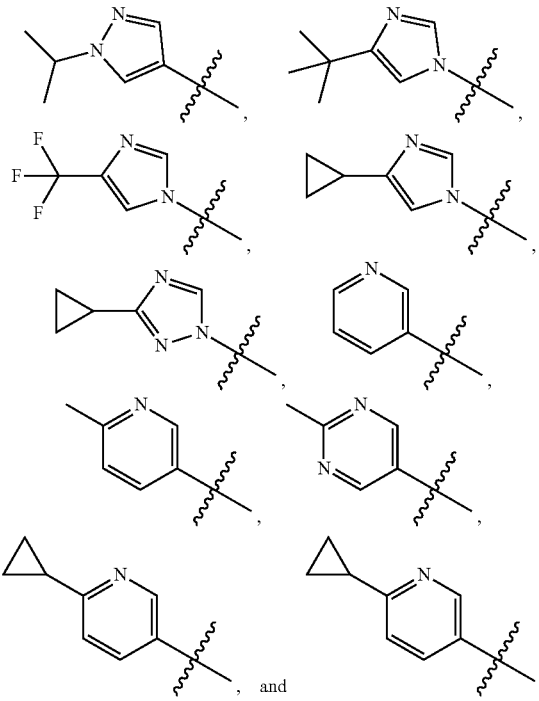

or
a pharmaceutically acceptable salt thereof; compositions, methods to treat liver disease and NASH.

25 Claims, No Drawings

(56) References Cited

OTHER PUBLICATIONS

International Search Report and Written Opinion of the International Searching Authority dated May 25, 2018 for Patent Application No. PCT/CN2017/100858, filed Sep. 7, 2017, 15 pages.
International Search Report and Written Opinion of the International Searching Authority dated Nov. 2, 2018 for Patent Application No. PCT/CN2018/100515, filed Aug. 14, 2018, 15 pages.

CYCLOBUTYL-IMIDAZOLIDINONE COMPOUNDS

This application claims foreign priority to PCT application nos. PCT/CN2017/100858 filed Sep. 7, 2017, and PCT/CN2018/100515 filed Aug. 14, 2018, the contents of each of which is incorporated herein by reference.

This invention provides cyclobutyl-imidazolidinone compounds or pharmaceutically acceptable salts thereof, and for use of the compounds in therapy. Cyclobutyl-Imidazolidinone compounds of this invention are inhibitors of apoptois signal-regulating kinase 1 (ASK1).

ASK1 is a member of the large mitogen-activated protein kinase kinase kinase ("MAP3K") family. ASK1 activation and signaling are associated with broad range of diseases. Compounds that inhibit ASK1 are desired for use in the treatment of ASK1 mediated conditions.

Compounds that inhibit ASK1 are desired for use in the treatment of Nonalcoholic steatohepatitis (NASH). Nonalcoholic steatohepatitis is a liver disease with an etiological constellation characterized by macrovesicular hepatic steatosis, inflammation hepatocyte ballooning and fibrosis. Currently, there is no approved pharmaceutical medicament specifically for the treatment of nonalcoholic steatohepatitis. There is a need for pharmaceutical medicaments to offer additional treatment options for patients suffering from nonalcoholic steatohepatitis.

U.S. Pat. No. 8,742,126 discloses 5-(4-cyclopropyl-1H-imidazol-1-yl)-N-(6-(4-isopropyl-4H-1,2,4-triazol-3-y-l) pyridin-2-yl)-2-fluoro-4-methylbenzamide as an ASK1 inhibitor.

U.S. Patent Application Publication No. US 2015/0342943 discloses a method of preventing and/or treating liver disease using an ASK1 inhibitor.

There is a need for compounds that have ASK1 inhibitory activity.

The present invention provides a compound of Formula I

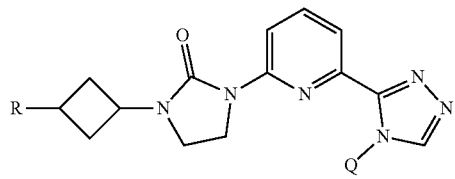

wherein

Q is selected from the group consisting of —CH(CH$_3$)$_2$ and

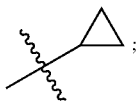 [SMILES: *C1CC1]

R is selected from the group consisting of

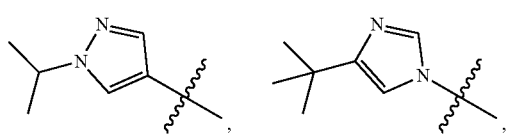

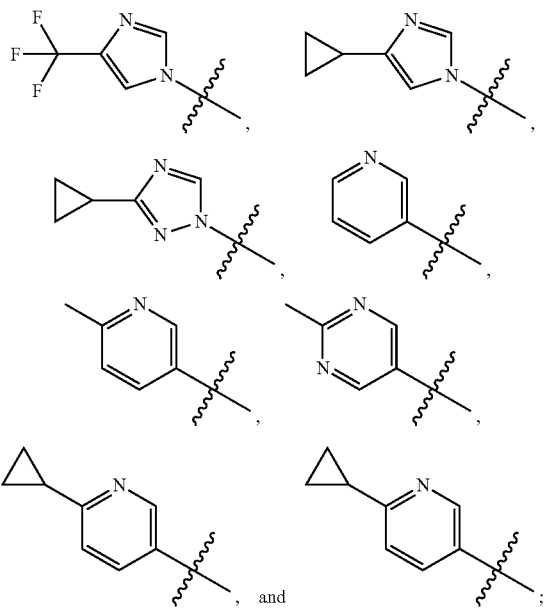

or a pharmaceutically acceptable salt thereof.

In an embodiment, R is selected from the group consisting of

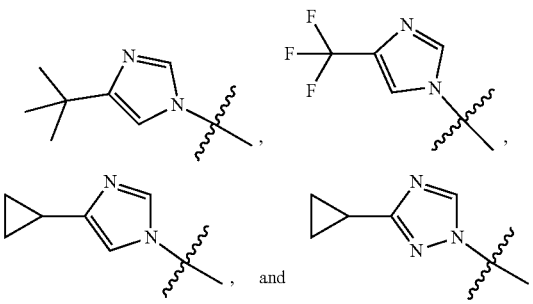

and Q is —CH(CH$_3$)$_2$.

In an embodiment, R is selected from the group consisting of

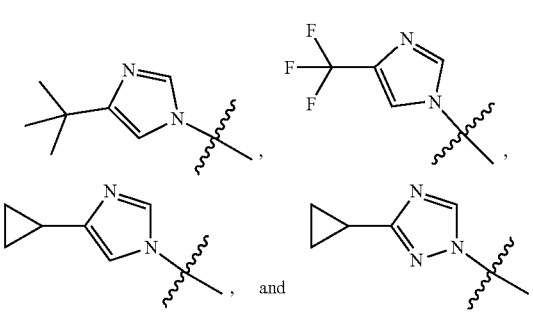

and Q is

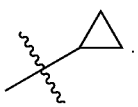 [SMILES: *C1CC1]

In an embodiment, R is

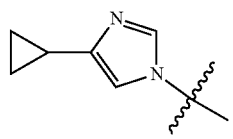 [SMILES: *n1cnc(C2CC2)c1]

and Q is —CH(CH$_3$)$_2$.

In an embodiment R is selected from the group consisting of

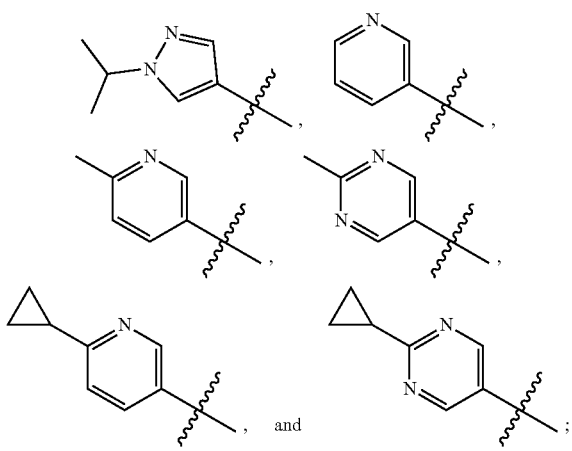

and

Q is —CH(CH$_3$)$_2$.

In an embodiment R is selected from the group consisting of

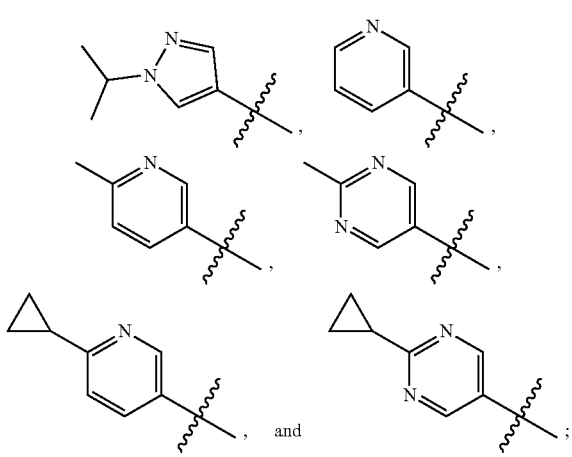

and Q is

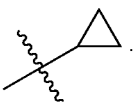 [SMILES: *C1CC1]

In an embodiment R is

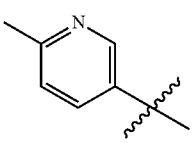 [SMILES: *c1ccc(C)nc1]

and Q is —CH(CH$_3$)$_2$

In an embodiment the compound of Formula I is 1-[3-(4-cyclopropylimidazol-1-yl)cyclobutyl]-3-[6-(4-isopropyl-1,2,4-triazol-3-yl)-2-pyridyl]imidazolidin-2-one, or a pharmaceutically acceptable salt thereof.

In an embodiment the compound of Formula I is 1-[6-(4-isopropyl-1,2,4-triazol-3-yl)-2-pyridyl]-3-[3-(6-methyl-3-pyridyl)cyclobutyl]imidazolidin-2-one, or a pharmaceutically acceptable salt thereof.

In an embodiment, the compound of Formula I is 1-(6-(4-isopropyl-4H-1,2,4-triazol-3-yl)pyridin-2-yl)-3-(3-(2-methylpyrimidin-5-yl)cyclobutyl)imidazolidin-2-one, or a pharmaceutically acceptable salt thereof.

The present invention provides a pharmaceutical composition comprising a compound of Formula I, or a pharmaceutically acceptable salt thereof, together with one or more pharmaceutically acceptable carriers, diluents, or excipients.

The present invention provides a method for treating a condition mediated by ASK1 activity comprising administering to the mammal in need of treatment, an effective amount of a compound of Formula I, or a pharmaceutically acceptable salt thereof. The present invention also provides a method for treating liver disease, comprising administering to a mammal in need thereof, an effective amount of a compound of Formula I, or a pharmaceutically acceptable salt thereof. The present invention provides a method for treating nonalcoholic steatohepatitis (NASH), comprising administering to a mammal in need thereof, an effective amount of a compound of Formula I, or a pharmaceutically acceptable salt thereof.

In another embodiment, the present invention provides a compound of Formula I, or a pharmaceutically acceptable salt thereof, for use in therapy. Further, provided is a compound of the present invention, or a pharmaceutically acceptable salt thereof or pharmaceutical composition, for use in the treatment of liver disease. Further, provided is a compound of the present invention, or a pharmaceutically acceptable salt thereof or pharmaceutical composition, for use in the treatment of NASH.

In another embodiment, provided is a compound of Formula I, or a pharmaceutically acceptable salt thereof, for use in the manufacture of a medicament for the treatment of liver disease. Preferably, the medicament is for the treatment of NASH.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington:*

*The Science and Practice of Pharmacy* (L. V. Allen, Editor, 22$^{nd}$ Edition, Pharmaceutical Press, 2012).

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002)

A human is a preferred mammal. As used herein, "patient" refers to a mammal in need of treatment. As used herein, the term "effective amount" or "therapeutically effective amount" of a compound refers to an amount, or a dosage, which is effective in treating a disorder or a disease, such as NASH, chronic kidney disease, or diabetic nephropathy as described herein. The attending diagnostician, as one skilled in the art, can readily determine an effective amount by the use of conventional techniques and by observing results obtained under analogous circumstances. In determining the effective amount or dose of a compound, a number of factors are considered, including but not limited to, the compound to be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

The pharmaceutical composition is administered to a patient in amounts effective to treat liver disease, more particularly, NASH. An appropriate amount or dose effective to treat a patient can be determined by a health care provider.

The terms "treatment" and "treating" as used herein are intended to refer to all processes wherein there may be a slowing, interrupting, arresting, controlling, or stopping of the progression of an existing disorder and/or symptoms thereof, but does not necessarily indicate a total elimination of all symptoms.

The term "liver disease" as used herein embraces liver conditions or symptoms associated with ASK1 mediation, for example, metabolic liver disease, steatosis, liver fibrosis, primary sclerosing cholangitis (PSC), cirrhosis, liver fibrosis, non-alcoholic fatty liver disease (NAFLD), nonalcoholic steatohepatitis (NASH), hepatic ischemia reperfusion injury, and primary biliary cirrhosis (PBC).

The term "pharmaceutically acceptable carrier, diluent, or excipients" means that the carrier, diluent, and excipients are pharmaceutically compatible with the other ingredients of the composition. In a particular embodiment, the pharmaceutical compositions are formulated as a tablet or capsule for oral administration. The tablet or capsule can include a compound of the present invention in an amount effective to treat liver disease, particularly NASH.

The abbreviations used herein are defined according to *Aldrichimica Acta*, Vol. 17, No. 1, 1984. Other abbreviations are defined as follows: "ACN" refers to acetonitrile; "ADP" refers to adenosine diphosphate; "ATP" refers to adenosine triphosphate; "boc" refers to tert-butoxycarbonyl; "BSA" refers to Bovine Serum Albumin; "DCM" refers to dichloromethane; DMEM" refers to Dulbecco's Modified Eagle's Medium; "DMF" refers to N,N-dimethylformamide; "DMP" refers to 1,1,1-triacetoxy-1,1-dihydro-1,2-benziodoxol-3(1H)-one, also known as Dess-Martin periodinane; "DMSO" refers to dimethylsulfoxide; "DTT" refers to dithiothreitol; "EtOH" refers to ethanol or ethyl alcohol; "FA" refers to formic acid; "FBS" refers to Fetal Bovine Serum; "HEK" refers to human embryonic kidney; "HPLC" refers to high performance liquid chromatography; "IC$_{50}$" refers to the concentration of an agent that produces 50% of the maximal inhibitory response possible for that agent; IPA" refers to isopropanol or isopropyl alcohol; "MAP" refers to mitogen-activated protein; "MeOH" refers to methanol or methyl alcohol; "MOPS" refers to (3-(N-morpholino)propanesulfonic acid); "NIS" refers to N-iodosuccinimide; "NP-40 refers to Tergitol-type NP-40 which is nonyl phenoxypolyethoxylethanoll; "pASK1" refers to phosphorylated ASK1; "Pd$_2$(dba)$_3$" refers to tris(dibenzylideneacetone)dipalladium(0); "PE" refers to petroleum ether; "SFC" refers to supercritical fluid chromatography; "TFA" refers to trifluoroacetic acid; "THF" refers to tetrahydrofuran; "TMSCN" refers to trimethylsilyl cyanide; "t$_{(R)}$" refers to retention time; "XantPhos" refers to 4,5-bis(diphenylphosphino)-9,9-dimethylxanthene.

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

The compounds of the present invention, or salts thereof, may be prepared by a variety of procedures known in the art, some of which are illustrated in the Preparations and Examples below. The specific synthetic steps for each of the routes described may be combined in different ways, to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

PREPARATIONS AND EXAMPLES

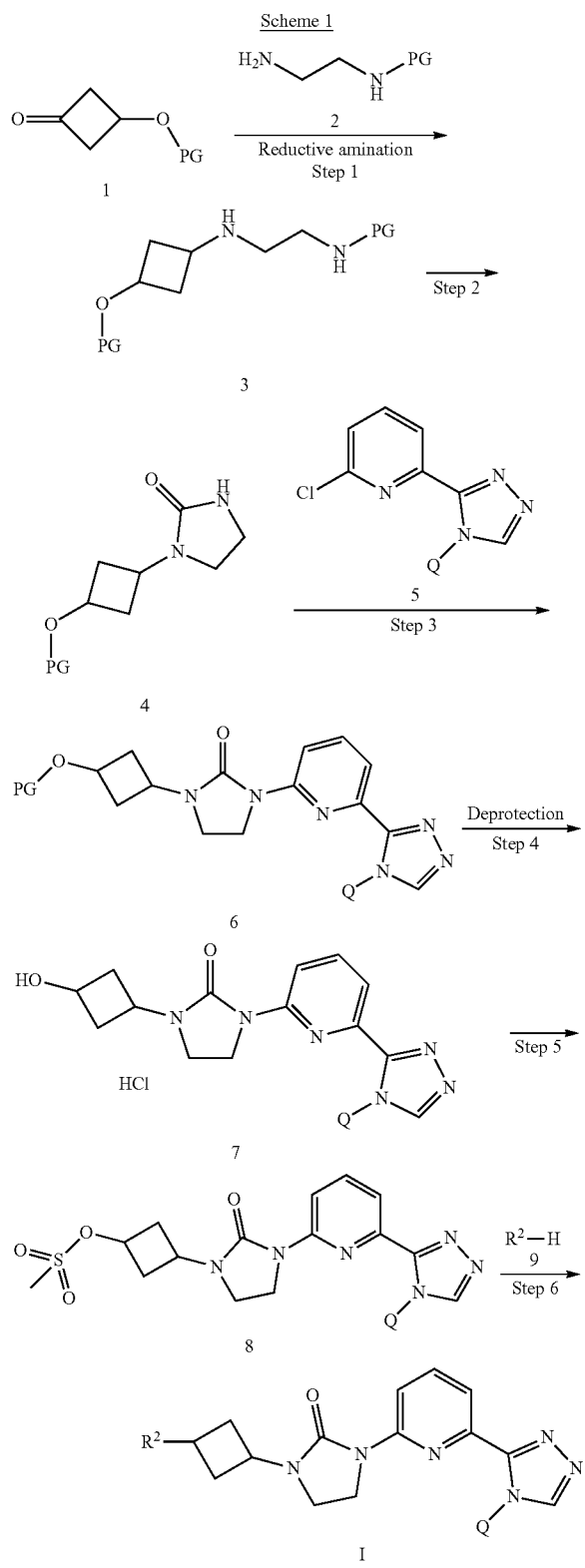

Compounds of this invention may be prepared as generally illustrated by Scheme 1 and using methods substantially as described by the Examples, when $R^2$ is selected from the group consisting of Scheme 1 depicts the synthesis of compounds of Formula I, wherein R is selected from the groups above denoted as $R^2$. "PG" is a protecting group developed for an amine or oxygen, such as carbamates and ethers. Such protecting groups are well known and appreciated in the art. A protected 3-cyclobutanone (1) can undergo a reductive amination as shown in Step 1. A reductive amination can be accomplished using conditions well known in the art. A solution of an amine (2) in a solvent such as DCM or MeOH, a ketone (1), a catalytic amount of acid such as acetic acid, and a reducing agent such as sodium triacetoxyborohydride can be stirred for an appropriate time to give compound (3). Other reducing agents known in the art which could be utilized are $NaBH_4$ or lithium borohydride. In Step 2, if the nitrogen protecting group of compound (3) is a carbamate such as boc or carboxybenzyl, the protected amine can be cyclized to the imidazolidin-2-one (4) with potassium tert-butoxide in a solvent such as THF and heating to about 60° C. Alternatively, the amine could be deprotected in one step under conditions well known in the art such as acidic conditions. Then cyclization could be accomplished in a second step using a coupling reagent such as 1,1'carbonyl-diimidazole (CDI) to give compound (4). A Buchwald-Hartwig amination can be accomplished to give compound (6) using palladium catalyzed cross-coupling of an amine with an aryl halide such as (5). Palladium cross-coupling conditions could include using a base such as $Cs_2CO_3$ in a solvent such as 1,4-dioxane with a phosphine ligand such as XantPhos and a catalyst such as $Pd_2(dba)_3$. The skilled artisan will recognize that there are a variety of conditions useful for facilitating such cross-coupling reactions. Suitable palladium reagents could include XantPhos Pd G2, cataCXium® A Pd G3, bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. Suitable bases could include potassium fluoride, sodium carbonate, potassium carbonate, lithium t-butoxide, or potassium phosphate tribasic monohydrate. If the oxygen protecting group of compound (6) is a benzyl ether, it can be deprotected in Step 4 under hydrogenation conditions well known in the art such as using palladium on carbon catalysts with hydrogen, a solvent such as MeOH, and a catalytic amount of acid such as HCl to give compound (7). The hydroxyl of compound 7 as an HCl salt or the neutral material of compound 7, (compound 11, shown in Scheme 2) can be reacted with methanesulfonyl chloride and an organic base such as triethylamine in a solvent such as DCM at a temperature of about 0° C. to give the methanesulfonate compound (8) as shown in Step 5. The methanesulfonyl of compound (8) can be displaced with R²—H (9) groups to give compounds of Formula I. For example, R²—H, compound (9) can be treated with a strong base such as sodium hydride at 0° C. to room temperature in a solvent such as DMF and stirred at room temperature. Compound (8) is then added and the mixture can be heated to about 80-90° C. for an appropriate time to give compounds of Formula I.

In an optional step, a pharmaceutically acceptable salt of a compound of Formula I can be formed by reaction of an appropriate free base of Formula I with an appropriate pharmaceutically acceptable acid in a suitable solvent under standard conditions. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I is readily converted to and may be isolated as a pharmaceutically acceptable salt.

Preparation 1 tert-Butyl N-[2-[(3-benzyloxycyclobutyl)amino]ethyl]carbamate

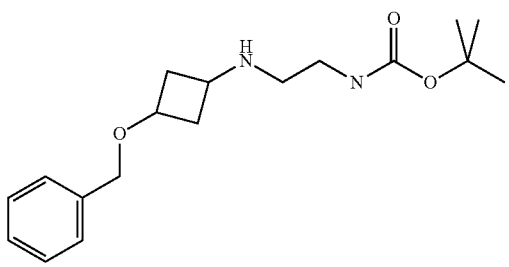 [SMILES: CC(C)(C)OC(=O)NCCNC1CC(OCc2ccccc2)C1]

A solution of 3-(benzyloxy)cyclobutanone (4.0 g, 22.0 mmol), N-boc-ethylenediamine (7.80 g, 48.7 mmol), DCM (50 mL), sodium triacetoxyborohydride (7.0 g, 33 mmol), and acetic acid (1.0 mL) are stirred at room temperature for 30 minutes. The residue is purified by silica gel flash chromatography, eluting with a gradient of 0% to 5% MeOH in DCM to give the title compound. ES/MS (m/z): 321.3 (M+1).

Preparation 2

1-(3-Benzyloxycyclobutyl)imidazolidin-2-one

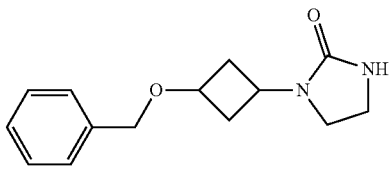 [SMILES: O=C1NCCN1C1CC(OCc2ccccc2)C1]

Potassium tert-butoxide (3.0 g, 26 mmol) is added a solution of tert-butyl N-[2-[(3-benzyloxycyclobutyl)amino]ethyl]carbamate (2.8 g, 8.7 mmol) in THF (200 mL) at room temperature under N₂. The mixture is stirred at 60° C. for 2 hours. The reaction is quenched by addition of water and the product is extracted with DCM (3×150 mL). The organic extracts are dried over Na₂SO₄, filtered, and concentrated in vacuo. The residue is purified by silica gel flash chromatography eluting with a gradient of 0% to 4% MeOH in DCM to give the title compound. ES/MS (m/z): 247.3 (M+1).

Preparation 3

1-(3-Benzyloxycyclobutyl)-3-[6-(4-isopropyl-1,2,4-triazol-3-yl)-2-pyridyl]imidazolidin-2-one

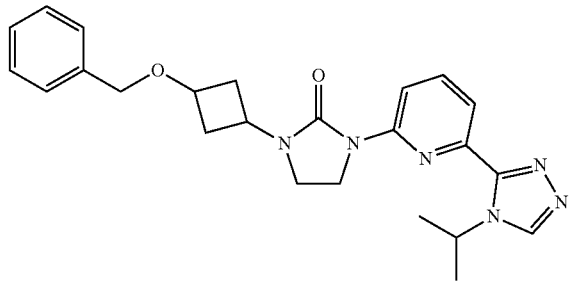 [SMILES: CC(C)n1cnnc1-c1cccc(N2CCN(C3CC(OCc4ccccc4)C3)C2=O)n1]

Cs₂CO₃ (4.0 g, 12.3 mmol) is added to a solution of 2-chloro-6-(4-isopropyl-1,2,4-triazol-3-yl)pyridine (0.95 g, 4.1 mmol) and 1-(3-benzyloxycyclobutyl)imidazolidin-2-one (1.0 g, 4.1 mmol) in 1,4-dioxane (20 mL). The mixture is degassed with a stream of N₂ for 5 minutes. XantPhos (0.48 g, 0.81 mmol) and Pd₂(dba)₃ (0.38 g, 0.41 mmol) are added sequentially and the resulting mixture is stirred at 130° C. for 4 hours under N₂. The mixture is diluted with DCM (2×75 mL) and washed sequentially with saturated brine (25 mL). The organic extracts are dried over Na₂SO₄, filtered, and evaporated to dryness. The crude material is purified by silica gel flash chromatography, eluting with a gradient of 0% to 50% EtOAc in hexanes to give the title compound. ES/MS (m/z): 433.3 (M+1).

Preparation 4

1-(3-Hydroxycyclobutyl)-3-[6-(4-isopropyl-1,2,4-triazol-3-yl)-2-pyridyl]imidazolidin-2-one; hydrochloride

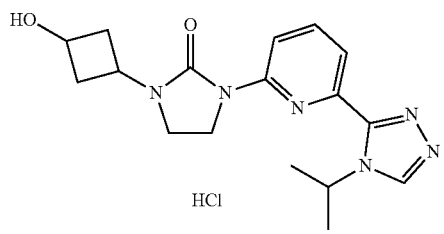 [SMILES: CC(C)n1cnnc1-c1cccc(N2CCN(C3CC(O)C3)C2=O)n1 ; Cl]

1-(3-Benzyloxycyclobutyl)-3-[6-(4-isopropyl-1,2,4-triazol-3-yl)-2-pyridyl]imidazolidin-2-one (9.0 g, 20.81 mmol), palladium (5 mass %) in Lindlar catalyst (3.0 g, 2.8 mmol), MeOH (150 mL) and hydrochloric acid (32 mass %) in H₂O (1.5 mL) are combined. The mixture is degassed with H₂ and stirred under balloon pressure of H₂ at room temperature for 12 hours. The mixture is filtered and concentrated to give the title compound, which is used without further purification. LC/MS (m/z): 343.3 (M+1-HCl).

Preparation 5

[3-[3-[6-(4-Isopropyl-1,2,4-triazol-3-yl)-2-pyridyl]-2-oxo-imidazolidin-1-yl]cyclobutyl]methanesulfonate

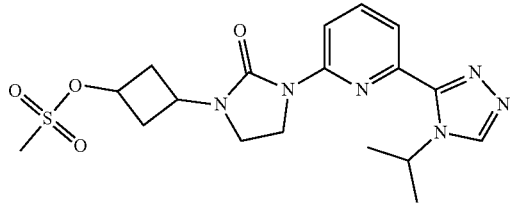 [SMILES: CC(C)n1cnnc1-c1cccc(N2CCN(C3CC(OS(C)(=O)=O)C3)C2=O)n1]

Methanesulfonyl chloride (0.747 g, 6.45 mmol) is added to a solution of 1-(3-hydroxycyclobutyl)-3-[6-(4-isopropyl-1,2,4-triazol-3-yl)-2-pyridyl]imidazolidin-2-one; (1.227 g, 3.23 mmol) and triethylamine (0.979 g, 9.68 mmol) in DCM (20 mL) at 0° C. The mixture is stirred at 0° C. for 15 minutes. The reaction is quenched with aq. NaHCO₃ (30 mL) and the product is extracted with DCM (2×50 mL). The organic extracts are dried over Na₂SO₄ and concentrated in vacuo. The residue is purified by silica gel flash chromatography, eluting with a gradient of 0% to 3% MeOH in DCM to give the title compound. ES/MS (m/z): 421.2 (M+1).

Alternative Preparation 5

[3-[3-[6-(4-Isopropyl-1,2,4-triazol-3-yl)-2-pyridyl]-2-oxo-imidazolidin-1-yl]cyclobutyl]methanesulfonate To a solution of 1-(3-hydroxycyclobutyl)-3-[6-(4-isopropyl-1,2,4-triazol-3-yl)-2-pyridyl]imidazolidin-2-one; hydrochloride (15.0 g, 41.62 mmol) and triethylamine (8.01 g, 79.18 mmol) in DCM (100 mL) at 0° C. is added methanesulfonyl chloride (11.45 g, 98.97 mmol). The mixture is stirred at room temperature for 2 hrs. The reaction is quenched by the addition of aq. NaHCO₃ (30 mL) solution and the product is extracted with DCM (150 mL). The organic layer is washed with brine (15 mL), dried over Na₂SO₄ and concentrated in vacuo. The residue is purified by silica gel flash chromatography, eluting with a gradient of 0% to 4% MeOH in DCM to give the title compound. ES/MS (m/z): 421.3 (M+1).

Preparation 6

1-[6-(4-Isopropyl-1,2,4-triazol-3-yl)-2-pyridyl]-3-(3-oxocyclobutyl)imidazolidin-2-one

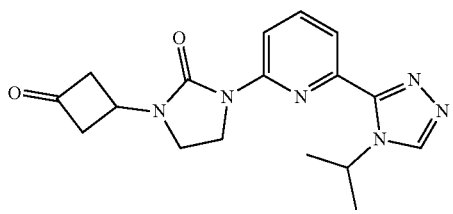 [SMILES: CC(C)n1cnnc1-c1cccc(N2CCN(C3CC(=O)C3)C2=O)n1]

DMP (6.9 g, 16.0 mmol) is added to a solution of 1-(3-hydroxycyclobutyl)-3-[6-(4-isopropyl-1,2,4-triazol-3-yl)-2-pyridyl]imidazolidin-2-one; hydrochloride (3.9 g, 11.0 mmol) in DCM (10 mL) at room temperature. The mixture is stirred at room temperature for 20 hours. The reaction is quenched with a sat. Na₂SO₃ and NaHCO₃ (30 mL) solution and the product is extracted with DCM (3×50 mL). The organic extracts are dried over Na₂SO₄ and concentrated in vacuo. The residue is purified by silica gel flash chromatography, eluting with a gradient of 0% to 2% MeOH in DCM to give the title compound. ES/MS (m/z): 341.3 (M+1).

Preparation 7

1-(3-Hydroxycyclobutyl)-3-[6-(4-isopropyl-1,2,4-triazol-3-yl)-2-pyridyl]imidazolidin-2-one

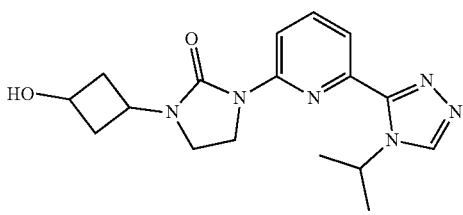 [SMILES: CC(C)n1cnnc1-c1cccc(N2CCN(C3CC(O)C3)C2=O)n1]

Sodium borohydride (249.0 mg, 6.45 mmol) is added to a solution of 1-[6-(4-isopropyl-1,2,4-triazol-3-yl)-2-pyridyl]-3-(3-oxocyclobutyl)imidazolidin-2-one (1.22 g, 3.226 mmol) in MeOH (10 mL) at 0° C. The mixture is stirred at 0° C. for 30 minutes. The reaction is quenched with aq. NaHCO₃ (10 mL) solution and the product is extracted with DCM (3×50 mL). The organic extracts are dried over Na₂SO₄ and concentrated in vacuo to give the title compound. ES/MS (m/z): 343.2 (M+1).

Scheme 2

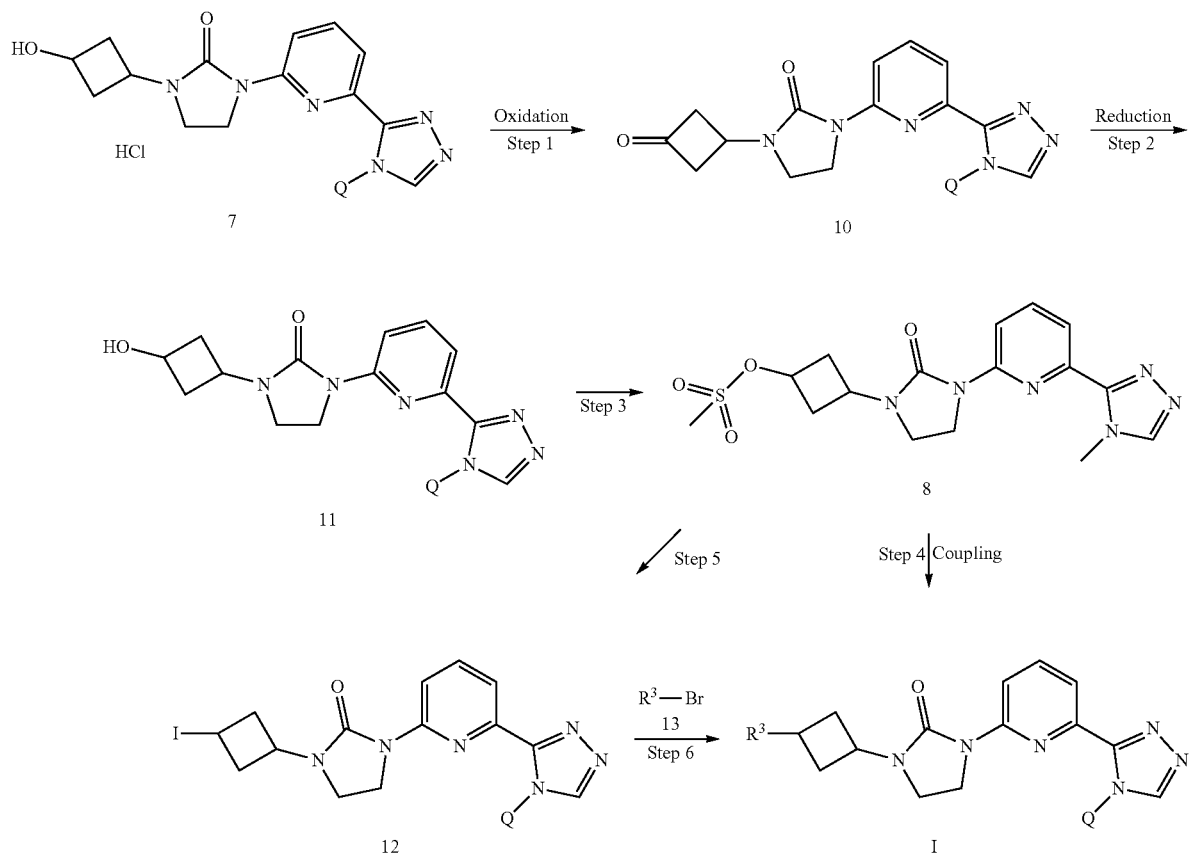

Compounds of this invention may be prepared as generally illustrated by Scheme 2 and using methods substantially described by the Examples, when R³ is selected from the group consisting of

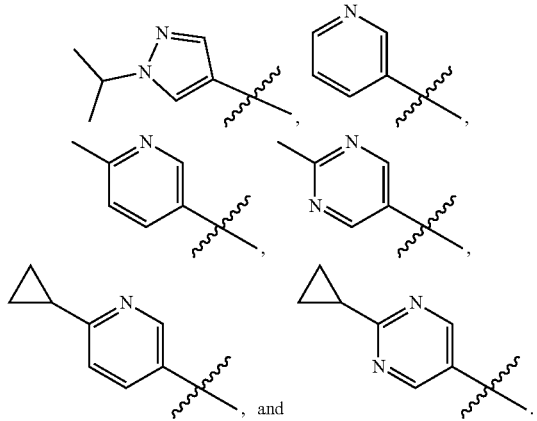, and

Scheme 2 depicts the synthesis of compounds of Formula I, wherein R is selected from the groups above denoted as R³ The hydroxyl of compound (7) prepared as an HCl salt and described in Scheme 1, Step 4, can be oxidized to the ketone using Dess-Martin periodinane. DMP is a mild oxidizing reagent commonly used to oxidize alcohols to ketones. DMP can be added to a solution of compound (7) in a solvent such as DCM at about room temperature to give the ketone compound (10) in Step 1. Compound (10) can be reduced back to the neutral hydroxyl compound (11) using a reducing agent such as sodium borohydride in a solvent such as DCM at a temperature of about 0° C. as shown in Step 2. The hydroxyl can then be reacted with methanesulfonyl chloride as described in Scheme 1, Step 5 to give compound (8). The methanesulfonyl of compound (8) can be displaced with iodine using a reagent such as sodium iodide in a solvent such as acetone and heated to about 80° C. to give compound (12). Compound (12) can be alkylated with Grignard-type reagents in a Grignard cross coupling reaction. N,N,N',N'-tetramethylethylenediamine (TMEDA) can be used as a readily removed ligand in an iron catalyzed coupling of Grignard reagents with activated alkyl halides such as compound (12) to give compounds of Formula I. Grignard reagents are well known in the art. For example, an isopropylmagnesium chloride-lithium chloride complex in THF is added to the appropriate R³—Br in a solvent such as THF at about 0° C. to form the appropriate Grignard type reagent. The Grignard solution is added to compound (12) in solution with a ligand such as TMEDA and a catalyst such as ferric acetylacetonate usually in a dropwise procedure at a temperature of about 0° C. The mixture is stirred at about room temperature to give compounds of Formula I.

Preparation 8

1-(3-Iodocyclobutyl)-3-[6-(4-isopropyl-1,2,4-triazol-3-yl)-2-pyridyl]imidazolidin-2-one

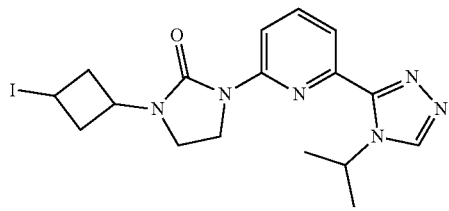 [SMILES: CC(C)n1cnnc1-c1cccc(N2CCN(C3CC(I)C3)C2=O)n1]

Sodium iodide (3.986 g, 26.59 mmol) is added to a solution of [3-[3-[6-(4-isopropyl-1,2,4-triazol-3-yl)-2-pyridyl]-2-oxo-imidazolidin-1-yl]cyclobutyl] methanesulfonate (1.177 g, 2.66 mmol) in acetone (10 mL) at room temperature. The mixture is stirred at 80° C. for 6 hrs. The reaction is concentrated; the solid is filtered, and is washed with DCM. The filtrate is concentrated in vacuo. The filtrate is purified by silica gel flash chromatography, eluting with a gradient of 0% to 3% MeOH in DCM to give the title compound. ES/MS (m/z): 452.8 (M+1).

Example 1

1-[3-(4-Cyclopropylimidazol-1-yl)cyclobutyl]-3-[6-(4-isopropyl-1,2,4-triazol-3-yl)-2-pyridyl]imidazolidin-2-one

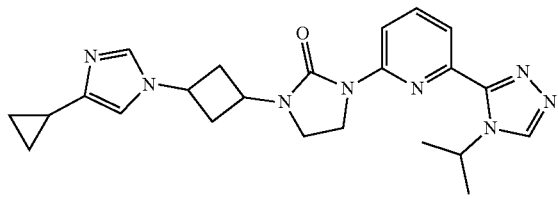 [SMILES: CC(C)n1cnnc1-c1cccc(N2CCN(C3CC(n4cnc(C5CC5)c4)C3)C2=O)n1]

Sodium hydride (60 mass %) in mineral oil (1.5 g, 39.0 mmol) is added to a solution of 4-cyclopropyl-1H-imidazole (2.8 g, 26.0 mmol) in DMF (50 mL) at room temperature. The mixture is stirred at room temperature for 30 minutes. [3-[3-[6-(4-Isopropyl-1,2,4-triazol-3-yl)-2-pyridyl]-2-oxo-imidazolidin-1-yl]cyclobutyl]methanesulfonate (5.7 g, 13 mmol) is added to the solution and the mixture is heated to 80° C. and stirred for 17 hours. The reaction is quenched with water (80 mL) and the product is extracted with DCM (3×150 mL). The organic extracts are washed with brine (30 mL), dried over $Na_2SO_4$, and concentrated in vacuo. The residue is purified by silica gel flash chromatography, eluting with a gradient of 0% to 4% MeOH in DCM followed by Preparative HPLC eluting with an isocratic system of 23% ACN (0.5% FA) in $H_2O$ (0.1% FA) for 41 min; column temperature: room temperature; flow rate: 30 mL/min, $t_{(R)}$=27.1 minutes (UV). The material is concentrated, dissolved in water, and lyophilized to give the title compound. ES/MS (m/z): 433.3 (M+1).

Example 2

1-[3-(4-Cyclopropylimidazol-1-yl)cyclobutyl]-3-[6-(4-isopropyl-1,2,4-triazol-3-yl)-2-pyridyl]imidazolidin-2-one, isomer 2

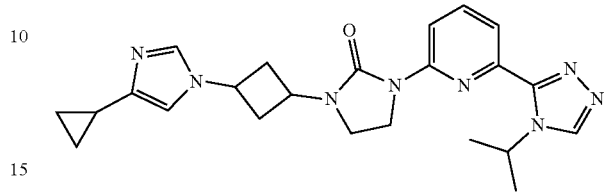

The mixture of 1-[3-(4-cyclopropylimidazol-1-yl)cyclobutyl]-3-[6-(4-isopropyl-1,2,4-triazol-3-yl)-2-pyridyl]imidazolidin-2-one (5.60 g, 12.9 mmol) is separated by SFC with the following conditions to give the second eluting compound as the title compound: column: OJ (250 mm*30 mm, 5 μm) eluting with 80% $CO_2$ and 20% EtOH (0.1% $NH_4OH$) to give the title compound ES/MS (m/z): 433.2 (M+1), LCMS: (Xtimate® C18 2.1*30 mm); eluting with a gradient of 10%-80% ACN (0.5% TFA) in $H_2O$ (0.5% TFA) 4 minute chromatography $t_{(R)}$=1.30 min, $^1$H NMR (400 MHz, CDCl$_3$) δ 8.39-8.26 (m, 2H), 7.91 (d, J=7.2 Hz, 1H), 7.79 (t, J=8.0 Hz, 1H), 7.43 (s, 1H), 6.81 (s, 1H), 5.61-5.47 (m, 1H), 4.82-4.62 (m, 2H), 4.07 (t, J=7.6 Hz, 2H), 3.64 (t, J=8.0 Hz, 2H), 3.02-2.84 (m, 2H), 2.74-2.58 (m, 2H), 1.85-1.80 (m, 1H), 1.56 (d, J=6.8 Hz, 6H), 0.88-0.80 (m, 2H), 0.79-0.71 (m, 2H).

Example 3

1-(6-(4-Isopropyl-4H-1,2,4-triazol-3-yl)pyridin-2-yl)-3-(3-(4-(trifluoromethyl)-1H-imidazol-1-yl)cyclobutyl)imidazolidin-2-one

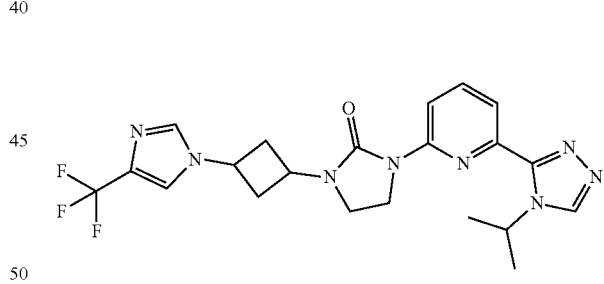

Sodium hydride (60 mass %) in mineral oil (41.6 mg, 1.04 mmol) is added to a solution of 4-(trifluoromethyl)-1H-imidazole (96.3 mg, 0.694 mmol) in DMF (5.0 mL) at 0° C. The mixture is stirred at room temperature for 30 minutes. [3-[3-[6-(4-Isopropyl-1,2,4-triazol-3-yl)-2-pyridyl]-2-oxo-imidazolidin-1-yl]cyclobutyl] methanesulfonate (162.0 mg, 0.347 mmol) is added at room temperature, the mixture is heated to 90° C., and stirred for 17 hours. The reaction is quenched with water (20 mL) and the product is extracted with DCM (3×40 mL). The organic extracts are dried over $Na_2SO_4$ and concentrated in vacuo. The residue is purified by HPLC under the following conditions column: SunFire® C18 5 μm, 30*100 mm, eluting with a gradient of 28%-43% of ACN (0.1% FA) in $H_2O$ (0.1% FA) over 10 minutes and stop at 17 minutes; flow rate: 30 mL/minutes. $t_{(R)}$ 7.5 minutes. The material is concentrated, dissolved in water, and lyophilized to give the title compound. ES/MS (m/z): 461.0 (M+1), $^1$H NMR (500 MHz, CDCl$_3$) δ 8.36 (s, 1H), 8.33 (d, J=8.3 Hz, 1H), 7.93 (d, J=7.5 Hz, 1H), 7.81 (t, J=8.0 Hz, 1H), 7.65 (s, 1H), 7.43 (s, 1H), 5.58-5.52 (m, 1H), 4.90-4.85 (m, 1H), 4.72-4.69 (m, 1H), 4.09 (t, J=8.0 Hz, 2H), 3.65 (t, J=8.0 Hz, 2H), 3.11-3.05 (m, 2H), 2.76-2.70 (m, 2H), 1.57 (d, J=7.0 Hz, 6H).

Example 4

1-[3-(3-Cyclopropyl-1,2,4-triazol-1-yl)cyclobutyl]-3-[6-(4-isopropyl-1,2,4-triazol-3-yl)-2-pyridyl]imidazolidin-2-one

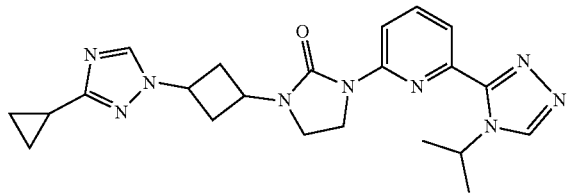 [SMILES: CC(C)n1cnnc1-c1cccc(N2CCN(C3CC(n4cnc(C5CC5)n4)C3)C2=O)n1]

Sodium hydride (60 mass %) in mineral oil (41.6 mg, 1.04 mmol) is added to a solution of 3-cyclopropyl-1H-1,2,4-triazole (79.7 mg, 0.694 mmol) in DMF (5.0 mL) at 0° C. The mixture is stirred at room temperature for 30 minutes. [3-[3-[6-(4-Isopropyl-1,2,4-triazol-3-yl)-2-pyridyl]-2-oxo-imidazolidin-1-yl]cyclobutyl] methanesulfonate (162.0 mg, 0.347 mmol) is added at room temperature, the mixture is heated to 90° C., and stirred for 17 hours. The reaction is quenched with water (20 mL) and the product is extracted with DCM (3×40 mL). The organic extracts are dried over Na$_2$SO$_4$ and concentrated in vacuo. The residue is purified by HPLC with the following conditions: column: SunFire C18 5μ, 30*100 mm, eluting with a gradient of 13-28% ACN (0.1% FA in water (0.1% FA) over 18 minutes; stop at 25 minutes; flow rate: 30 mL/minute, t$_{(R)}$ 9.0 min. The material is concentrated, dissolved in water, and lyophilized to give the title compound. ES/MS (m/z): 434.0 (M+1), $^1$H NMR (500 MHz, CDCl$_3$) δ 8.20-8.19 (m, 1H), 8.18 (s, 1H), 7.80 (s, 1H), 7.76 (d, J=7.5 Hz, 1H), 7.64 (t, J=8.0 Hz, 1H), 5.45-5.38 (m, 1H), 4.76-4.67 (m, 2H), 3.92 (t, J=8.0 Hz, 2H), 3.49 (t, J=8.0 Hz, 2H), 2.86-2.80 (m, 2H), 2.76-2.68 (m, 2H), 1.96-1.90 (m, 1H), 1.41 (d, J=7.0 Hz, 6H), 0.84-0.82 (m, 4H).

Example 5

1-(3-(4-(tert-Butyl)-1H-imidazol-1-yl)cyclobutyl)-3-(6-(4-isopropyl-4H-1,2,4-triazol-3-yl)pyridin-2-yl)imidazolidin-2-one

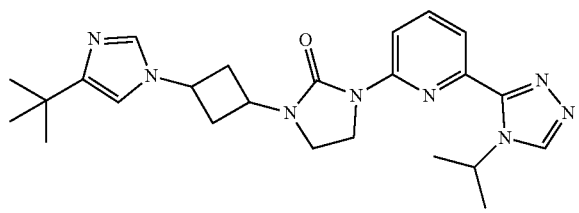 [SMILES: CC(C)n1cnnc1-c1cccc(N2CCN(C3CC(n4cnc(C(C)(C)C)c4)C3)C2=O)n1]

Sodium hydride (60 mass %) in mineral oil (28.5 mg, 0.713 mmol) is added to a solution of 4-tert-butyl-1H-imidazole (59.1 mg, 0.476 mmol) in DMF (10.0 mL) at 0° C. The mixture is stirred at room temperature for 30 minutes. [3-[3-[6-(4-Isopropyl-1,2,4-triazol-3-yl)-2-pyridyl]-2-oxo-imidazolidin-1-yl]cyclobutyl] methanesulfonate (100.0 mg, 0.238 mmol) is added at room temperature, the mixture is heated to 80° C., and stirred for 2 hours. The reaction mixture is concentrated in vacuo. The residue is purified by HPLC with the following conditions column: SunFire® C18 5 μm, 30*100 mm, eluting with a gradient of 10-25% ACN (0.1% FA) in water (0.1% FA) over 10 minutes; stop at 17 minutes; flow rate: 30 mL/minute; t$_{(R)}$ 18.2 minutes. The material is concentrated, dissolved in water, and lyophilized to give the title compound. ES/MS (m/z): 449.4 (M+1), $^1$H NMR (500 MHz, CD$_3$OD) δ 8.87 (s, 1H), 8.37 (d, J=7.5 Hz, 1H), 8.23 (s, 1H), 7.92 (t, J=7.5 Hz, 1H), 7.76 (d, J=7.5 Hz, 1H), 7.27 (s, 1H), 5.62-5.57 (m, 1H), 4.96-4.93 (m, 1H), 4.82-4.76 (m, 1H), 4.18 (t, J=8.0 Hz, 2H), 3.79 (t, J=8.0 Hz, 2H), 3.07-3.01 (m, 2H), 2.91-2.77 (m, 2H), 1.63-1.61 (m, 6H), 1.35 (s, 9H).

Example 6

1-[3-(1-Isopropylpyrazol-4-yl)cyclobutyl]-3-[6-(4-isopropyl-1,2,4-triazol-3-yl)-2-pyridyl]imidazolidin-2-one

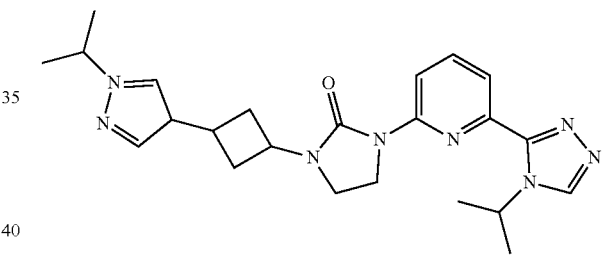

Isopropylmagnesium chloride-lithium chloride complex (1.3 mol/L) in THF (2.6 mL, 3.36 mmol is added to a solution of 4-bromo-1-isopropyl-pyrazole (327.5 mg, 1.680 mmol) in THF (2.0 mL) at 0° C. under N$_2$. The mixture is stirred at room temperature for 4 hours. The mixture is added dropwise to a solution of 1-(3-iodocyclobutyl)-3-[6-(4-isopropyl-1,2,4-triazol-3-yl)-2-pyridyl]imidazolidin-2-one (200.0 mg, 0.42 mmol), ferric acetylacetonate (156.2 mg, 0.42 mmol) and N,N,N',N'-tetramethylethylenediamine (0.16 mL, 1.05 mmol) in THF (2.0 mL) at 0° C. The mixture is stirred at room temperature for 1 hour. The reaction is quenched with water (20 mL) and the product is extracted with DCM (3×40 mL). The organic extracts are dried over Na$_2$SO$_4$. concentrated in vacuo, and the residue is purified by HPLC with the following conditions: column: SunFire® C18 5μ, 30*100 mm, eluting with a gradient of 23%-38% ACN (0.1% FA) in water (0.1% FA) over 18 minutes; stop at 25 minutes; flow rate: 30 mL/minute; t$_{(R)}$ 17.2 minutes. The material is concentrated, dissolved in water, and lyophilized to give the title compound. ES/MS (m/z): 435.0 (M+1), $^1$H NMR (500 MHz, CDCl$_3$) δ 8.36-8.34 (m, 2H), 7.89 (d, J=7.5 Hz, 1H), 7.78 (t, J=7.5 Hz, 1H), 7.43 (s, 1H), 7.35 (s, 1H), 5.61-5.56 (m, 1H), 4.86-4.79 (m, 1H), 4.51-4.44 (m, 1H), 4.06 (t, J=8.0 Hz, 2H), 3.66 (t, J=8.0 Hz, 2H), 3.49-3.32 (m, 1H), 2.76-2.67 (m, 2H), 2.31-2.21 (m, 2H), 1.57 (d, J=7.0 Hz, 6H), 1.52 (d, J=7.0 Hz, 6H).

Example 7

1-[6-(4-Isopropyl-1,2,4-triazol-3-yl)-2-pyridyl]-3-[3-(6-methyl-3-pyridyl)cyclobutyl]imidazolidin-2-one

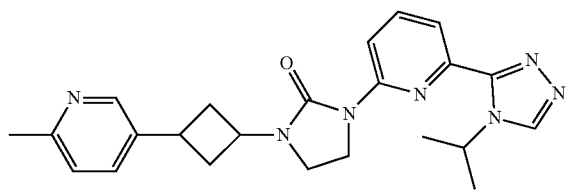 [SMILES: Cc1ccc(C2CC(N3CCN(c4cccc(-c5nncn5C(C)C)n4)C3=O)C2)cn1]

Isopropylmagnesium chloride-lithium chloride complex (1.3 mol/L) in THF (1.9 mL, 2.52 mmol) is added to a solution of 5-bromo-2-methyl-pyridine (223.5 mg, 1.260 mmol) in THF (5.0 mL) at 0° C. under $N_2$. The mixture is stirred at room temperature for 4.0 hours. The mixture is added dropwise to the solution of 1-(3-iodocyclobutyl)-3-[6-(4-isopropyl-1,2,4-triazol-3-yl)-2-pyridyl]imidazolidin-2-one (200.0 mg, 0.42 mmol), ferric acetylacetonate (31.2 mg, 0.084 mmol) and N,N,N',N'-tetramethylethylene diamine (0.16 mL, 1.05 mmol) in THF (5.0 mL) at 0° C. The mixture is stirred at room temperature for 1 hour. The reaction is quenched with water (20 mL) and the product is extracted with DCM (3×40 mL). The organic extracts are dried over $Na_2SO_4$, concentrated in vacuo, and purified by silica gel flash chromatography, eluting with a gradient of 0% to 6% MeOH in DCM to give the title compound. ES/MS (m/z): 418.1 (M+1).

Example 8

1-[6-(4-Isopropyl-1,2,4-triazol-3-yl)-2-pyridyl]-3-[3-(6-methyl-3-pyridyl)cyclobutyl]imidazolidin-2-one, isomer 2

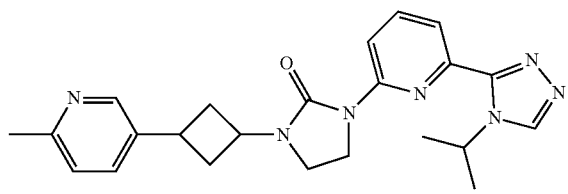 [SMILES: Cc1ccc(C2CC(N3CCN(c4cccc(-c5nncn5C(C)C)n4)C3=O)C2)cn1]

1-[6-(4-isopropyl-1,2,4-triazol-3-yl)-2-pyridyl]-3-[3-(6-methyl-3-pyridyl)cyclobutyl]imidazolidin-2-one (60.0 mg, 0.133 mmol) is separated by SFC to give the second eluting compound as the title compound: column: AD (250 mm*30 mm, 5 μm), eluting an isocratic system of 60% $CO_2$ and 40% IPA (0.1% $NH_4OH$); flow rate: 50 mL/minute to give the title compound. ES/MS (m/z): 418.1 (M+1), LCMS: column: (Xtimate C18 2.1*30 mm); eluting with a gradient of 10% to 80% IPA in $H_2O$ (0.1% $NH_3$) over 4 minutes; $t_{(R)}$=1.393 minutes, $^1$H NMR (400 MHz, CDCl$_3$) δ 8.41 (s, 1H), 8.37-8.30 (m, 2H), 7.88 (d, J=7.2 Hz, 1H), 7.77 (d, J=8.0 Hz, 1H), 7.59 (dd, J=2.4, 8.0 Hz, 1H), 7.15 (d, J=8.0 Hz, 1H), 5.63-5.50 (m, 1H), 4.82-4.70 (m, 1H), 4.07 (t, J=7.6 Hz, 2H), 3.69 (t, J=8.4 Hz, 2H), 3.56-3.45 (m, 1H), 2.86-2.74 (m, 2H), 2.54 (s, 3H), 2.50-2.41 (m, 2H), 1.56 (d, J=6.4 Hz, 6H).

Example 9

1-(6-(4-Isopropyl-4H-1,2,4-triazol-3-yl)pyridin-2-yl)-3-(3-(2-methylpyrimidin-5-yl)cyclobutyl)imidazolidin-2-one, isomer 2

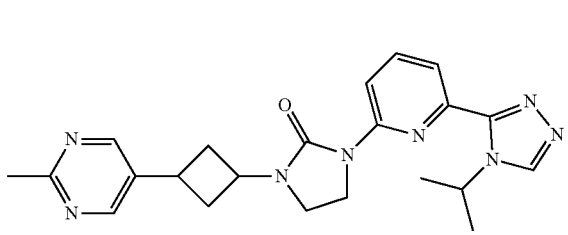 [SMILES: Cc1ncc(C2CC(N3CCN(c4cccc(-c5nncn5C(C)C)n4)C3=O)C2)cn1]

A solution of (2-methylpyrimidin-5-yl)boronic acid (0.236 g, 1.68 mmol) nickel iodide (0.0328 g, 0.105 mmol), trans-2-amino cyclohexanol (0.0123 g, 0.105 mmol), sodium bis(trimethylsilyl)amide (0.122 g, 0.630 mmol) in 2-propanol (4 mL) is stirred at room temperature under nitrogen for 5 minutes. 1-(3-Iodocyclobutyl)-3-[6-(4-isopropyl-1,2,4-triazol-3-yl)-2-pyridyl]imidazolidin-2-one (100 mg, 0.210 mmol) is added to the mixture and the mixture is stirred at 120° C. under microwave conditions for 12 hours. The reaction is quenched with water and extracted with DCM (3×). The combined organic extracts are dried over $Na_2SO_4$, filtered, and concentrated to dryness. The residue is purified by silica gel flash chromatography eluting with 5% MeOH in DCM to give the title product (80 mg, 86.5%) as a light yellow solid with a cis and trans ratio of about 2:1. ES/MS (m/z): 419 (M+H).

1-(6-(4-Isopropyl-4H-1,2,4-triazol-3-yl)pyridin-2-yl)-3-(3-(2-methylpyrimidin-5-yl)cyclobutyl)imidazolidin-2-one is separated by SFC to give the second eluting compound as the title compound: column: AD (250 mm*30 mm, 5 μm), eluting with an isocratic system of 70% $CO_2$ and 30% EtOH (0.1% $NH_4OH$); flow rate: 50 mL/minute to give the title compound (16.1 mg, 20.5%) as a white solid. ES/MS (m/z), 441.3 (M+Na)$^+$, LCMS: column: (Xtimate C18 2.1*30 mm); eluting with a gradient of 10% to 80% IPA in $H_2O$ (0.1% $NH_3$) over 4 minutes; $t_{(R)}$=1.666 minutes, $^1$H NMR (400 MHz, CDCl$_3$) δ 8.63 (s, 2H), 8.40-8.30 (m, 2H), 7.91 (d, J=7.2 Hz, 1H), 7.84-7.75 (m, 1H), 5.65-5.49 (m, 1H), 4.82-4.71 (m, 1H), 4.15-4.03 (m, 2H), 3.75-3.64 (m, 2H), 3.58-3.46 (m, 1H), 2.94-2.81 (m, 2H), 2.75 (s, 3H), 2.56-2.47 (m, 2H), 1.58 (d, J=6.8 Hz, 6H).

Biological Assays

ASK1 Inhibitor Effect Determined by ASK1 Enzymatic Assay

The purpose of this assay is to determine the effect of ASK1 inhibitors on the production of ADP by ASK1. The recombinant human ASK1 (hASK1) catalytic domain tagged with Glutathione S-transferase is used, and histidine-tagged full-length human MAP kinase kinase 6 (MKK6) and ATP are the substrate and cofactor, respectively.

The assay is done using an ADP-Glo™ Kinase Assay Kit (Promega, Catalog #V9102) according to the manufacturer's protocol with the following modifications. Briefly, hASK1

(0.25 nM) and MKK6 (300 nM) in a buffer (10 mM MOPS pH 7.0; 10 mM Mg-Acetate; 1 mM DTT; 0.025% NP-40; 0.05% BSA; 1.5% glycerol) are incubated with ASK1 inhibitors at varying concentrations ranging from 10.00 µM to 0.17 nM for 15 minutes, followed by incubation with ATP (100 µM) for 30 minutes at room temperature. ADP-Glo™ Reagent is added to terminate the kinase reaction and deplete the remaining ATP. The Kinase Detection Reagent is then added to convert ADP to ATP. The newly synthesized ATP is measured using a luciferase/luciferin reaction, and the luminescence determined by Envision (PerkinElmer). The luminescence intensities are analyzed by GeneData, and fit to a 4 parameter dose response-inhibitor logistics curve to determine $IC_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle for 100% and 0% inhibition, respectively.

Compounds of the Examples herein are tested essentially as described above and shown in Table 1.

TABLE 1

| Example # | hASK1 $IC_{50}$ (nM) | Efficacy (%) |
|---|---|---|
| 2 | 1.47 ± 0.60, n = 14 | 100 |
| 3 | 2.80 ± 0.97, n = 6 | 100 |
| 4 | 2.56 ± 0.68, n = 4 | 100 |
| 5 | 1.84 ± 0.64, n = 4 | 100 |
| 6 | 2.17 ± 0.45, n = 2 | 100 |
| 8 | 5.26 ± 0.72, n = 4 | 100 |
| 9 | 6.21 ± 4.18, n = 7. | 100 |

Mean ± standard deviation

These results indicate that the Examples tested inhibit ASK1 enzymatic activity as shown in Table 1.

ASK1 Inhibitor Effect Determined by ASK1 Autophosphorylation (Thr838) Assay

The purpose of this assay is to determine the effect of ASK1 inhibitors on $H_2O_2$-stimulated ASK1 autophosphorylation at Thr838 in HEK293 cells overexpressing human ASK1.

HEK293 cells overexpressing human influenza hemagglutinin- (HA-) tagged full length human ASK1 are maintained in DMEM supplemented with 10% FBS at 37° C. and 5% $CO_2$. For the assay, the cells are plated in matrigel-coated 96-well plates (25,000 cells/well) and incubated overnight. The cells are treated with ASK1 inhibitors at varying concentrations ranging from 10.00 µM to 0.17 nM for 1 hour, followed by stimulation with 1 mM $H_2O_2$ for 10 minutes. The cells are then lysed with Homogeneous Time-Resolved Fluorescence (HTRF®) lysis buffer (Cisbio, Catalog #64KL1FDF) containing phosphatase inhibitors (ThermoFisher, Catalog #78430). pASK1 is quantified by HTRF®, using an anti-HA and anti-pASK1 (Thr838) antibody pair customized by Cisbio, on Envision (PerkinElmer) with emission and excitation wavelengths of 620 and 665 nm, respectively. The ratios of fluorescence intensities at 665 nm and 620 nm are analyzed by GeneData, and fit to a 4 parameter dose response-inhibitor logistics curve to determine $IC_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle as 100% and 0% inhibition, respectively.

Compounds of the Examples herein are tested essentially as described and the results are shown in Table 2.

TABLE 2

| Example # | HEK pASK1 $IC_{50}$ (nM) | Efficacy (%) |
|---|---|---|
| 2 | 48.8 ± 19.1, n = 3 | 105 |
| 3 | 126 | 98.5 |
| 4 | 108 | 99 |
| 6 | 27.1 | 102 |
| 8 | 235 | 97.5 |

Mean ± standard deviation

These results support that the Example compounds as shown in Table 2 above inhibit $H_2O_2$-stimulated ASK1 autophosphorylation at Thr838 in HEK293 cells.

We claim:
1. A compound of the formula

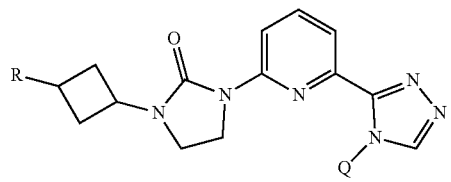

wherein:

Q is selected from the group consisting of —$CH(CH_3)_2$ and

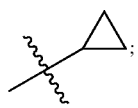 [SMILES: *C1CC1]

and

R is selected from the group consisting of

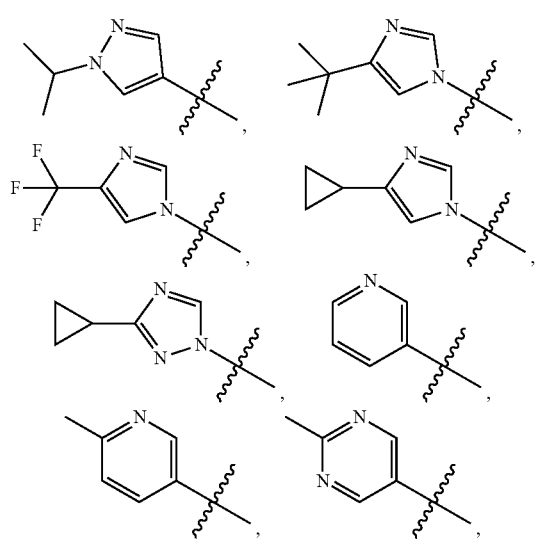

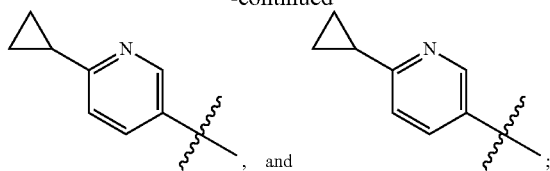

, and ;

or a pharmaceutically acceptable salt thereof.

2. The compound of claim 1, or a pharmaceutically acceptable salt thereof, wherein: Q is —CH(CH$_3$)$_2$.

3. The compound of claim 1, or a pharmaceutically acceptable salt thereof, wherein: R is selected from the group consisting of

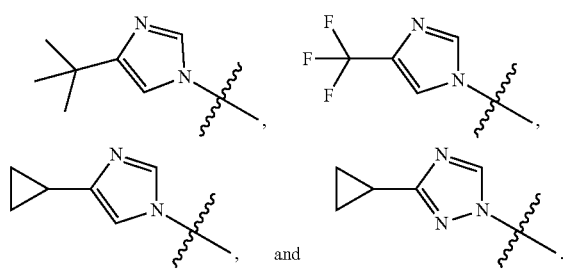

4. The compound of claim 3, or a pharmaceutically acceptable salt thereof, wherein: R is selected from the group consisting of

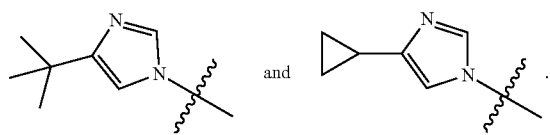

5. The compound of claim 1, or a pharmaceutically acceptable salt thereof, wherein: R is selected from the group consisting of

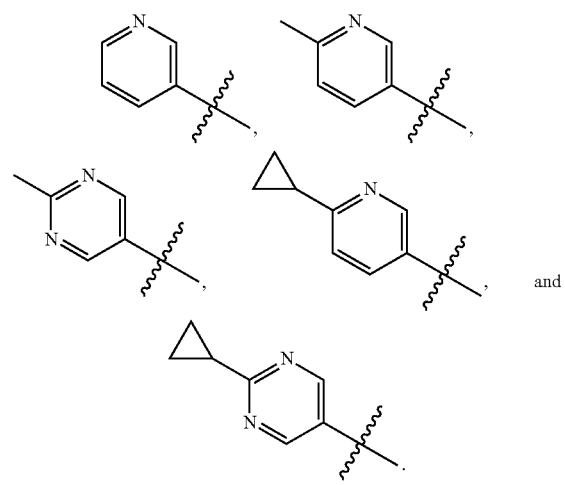

6. The compound of claim 5, or a pharmaceutically acceptable salt thereof, wherein: R is selected from the group consisting of 7. The compound of claim 1, which is: 1-[6-(4-isopropyl-1,2,4-triazol-3-yl)-2-pyridyl]-3-[3-(6-methyl-3-pyridyl)cyclobutyl]imidazolidin-2-one, or a pharmaceutically acceptable salt thereof.

8. The compound of claim 1, which is: 1-[3-(4-cyclopropylimidazol-1-yl)cyclobutyl]-3-[6-(4-isopropyl-1,2,4-triazol-3-yl)-2-pyridyl]imidazolidin-2-one, or a pharmaceutically acceptable salt thereof.

9. The compound of claim 1, which is: 1-(3-(4-(tert-butyl)-1H-imidazol-1-yl)cyclobutyl)-3-(6-(4-isopropyl-4H-1,2,4-triazol-3-yl)pyridin-2-yl)imidazolidin-2-one, or a pharmaceutically acceptable salt thereof.

10. The compound of claim 1, which is: 1-(6-(4-isopropyl-4H-1,2,4-triazol-3-yl)pyridin-2-yl)-3-(3-(2-methylpyrimidin-5-yl)cyclobutyl)imidazolidin-2-one, or a pharmaceutically acceptable salt thereof.

11. A pharmaceutical composition comprising the compound of claim 1, or a pharmaceutically acceptable salt thereof, and at least one pharmaceutically acceptable carrier, diluent, or excipient.

12. A method for treating nonalcoholic steatohepatitis (NASH) in a mammal in need thereof, comprising administering to an effective amount of the compound of claim 1, or a pharmaceutically acceptable salt thereof, to the mammal.

13. The compound of claim 2, or a pharmaceutically acceptable salt thereof, wherein: R is selected from the group consisting of

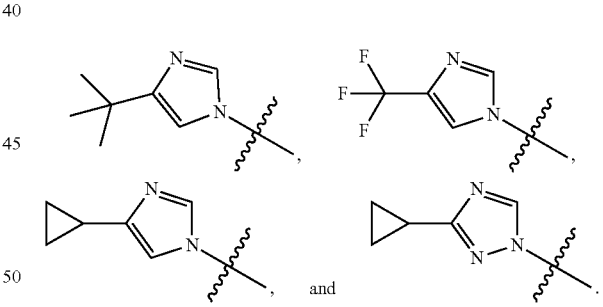

14. The compound of claim 13, or a pharmaceutically acceptable salt thereof, wherein: R is selected from the group consisting of

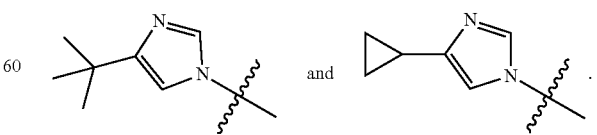

15. The compound of claim 2, or a pharmaceutically acceptable salt thereof, wherein: R is selected from the group consisting of:

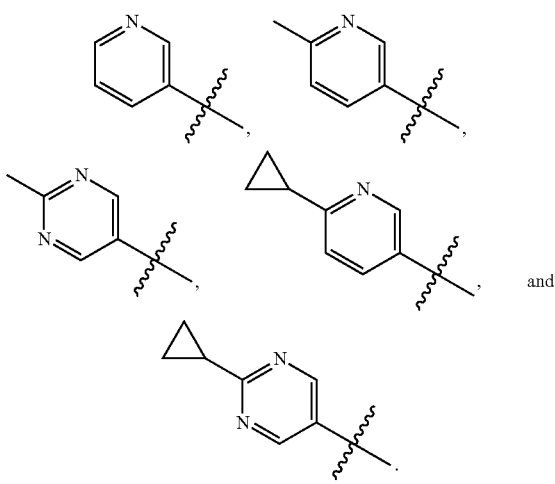

16. The compound of claim 15, or a pharmaceutically acceptable salt thereof, wherein: R is selected from the group consisting of

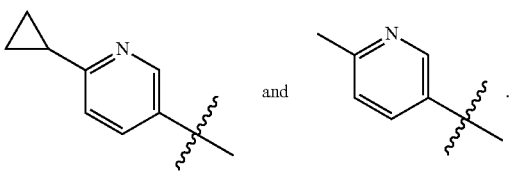

17. The method of claim 12, wherein the mammal is a human.

18. The method of claim 12, wherein the compound is:
1-[6-(4-isopropyl-1,2,4-triazol-3-yl)-2-pyridyl]-3-[3-(6-methyl-3-pyridyl)cyclobutyl]imidazolidin-2-one,
or a pharmaceutically acceptable salt thereof.

19. The method of claim 12, wherein the compound is:
1-[3-(4-cyclopropylimidazol-1-yl)cyclobutyl]-3-[6-(4-isopropyl-1,2,4-triazol-3-yl)-2-pyridyflimidazolidin-2-one,
or a pharmaceutically acceptable salt thereof.

20. The method of claim 12, wherein the compound is:
1-(3-(4-(tert-butyl)-1H-imidazol-1-yl)cyclobutyl)-3-(6-(4-isopropyl-4H-1,2,4-triazol-3-yl)pyridin-2-yl)imidazolidin-2-one,
or a pharmaceutically acceptable salt thereof.

21. The method of claim 12, wherein the compound is:
1-(6-(4-isopropyl-4H-1,2,4-triazol-3-yl)pyridin-2-yl)-3-(3-(2-methylpyrimidin-5-yl)cyclobutyl)imidazolidin-2-one,
or a pharmaceutically acceptable salt thereof.

22. The pharmaceutical composition of claim 11, wherein the compound is:
1-[6-(4-isopropyl-1,2,4-triazol-3-yl)-2-pyridyl]-3-[3-(6-methyl-3-pyridyl)cyclobutyl]imidazolidin-2-one,
or a pharmaceutically acceptable salt thereof.

23. The pharmaceutical composition of claim 11, wherein the compound is:
1-[3-(4-cyclopropylimidazol-1-yl)cyclobutyl]-3-[6-(4-isopropyl-1,2,4-triazol-3-yl)-2-pyridyflimidazolidin-2-one,
or a pharmaceutically acceptable salt thereof.

24. The pharmaceutical composition of claim 11, wherein the compound is:
1-(3-(4-(tert-butyl)-1H-imidazol-1-yl)cyclobutyl)-3-(6-(4-isopropyl-4H-1,2,4-triazol-3-yl)pyridin-2-yl)imidazolidin-2-one,
or a pharmaceutically acceptable salt thereof.

25. The pharmaceutical composition of claim 11, wherein the compound is:
1-(6-(4-isopropyl-4H-1,2,4-triazol-3-yl)pyridin-2-yl)-3-(3-(2-methylpyrimidin-5-yl)cyclobutyl)imidazolidin-2-one,
or a pharmaceutically acceptable salt thereof.

* * * * *